(12) United States Patent
Lan et al.

(10) Patent No.: US 8,367,341 B2
(45) Date of Patent: Feb. 5, 2013

(54) METHOD FOR DETECTION OF GENETICALLY MODIFIED MAIZE BT11

(75) Inventors: Qingkuo Lan, Tianjin (CN); Yong Wang, Tianjin (CN); Yi Cheng, Tianjin (CN); Xin Zhao, Tianjin (CN); Zhu Zhu, Tianjin (CN)

(73) Assignee: Central Lab of Tianjin Academy of Agricultural Sciences, Tianjin (CN)

( * ) Notice: Subject to any disclaimer, the term of this patent is extended or adjusted under 35 U.S.C. 154(b) by 421 days.

(21) Appl. No.: 12/673,322

(22) PCT Filed: Apr. 17, 2009

(86) PCT No.: PCT/CN2009/000410
§ 371 (c)(1),
(2), (4) Date: Feb. 12, 2010

(87) PCT Pub. No.: WO2010/022579
PCT Pub. Date: Mar. 4, 2010

(65) Prior Publication Data
US 2012/0088243 A1    Apr. 12, 2012

(30) Foreign Application Priority Data
Aug. 26, 2008 (CN) .......................... 2008 1 0054283

(51) Int. Cl.
*C12Q 1/68* (2006.01)
*C12P 19/34* (2006.01)
*C07H 1/00* (2006.01)
*C07H 5/04* (2006.01)
*C07H 19/00* (2006.01)
*C07H 21/02* (2006.01)
*C07H 21/04* (2006.01)

(52) U.S. Cl. ...... 435/6.12; 435/6.1; 435/6.11; 536/1.11; 536/18.7; 536/22.1; 536/23.1; 536/24.3; 536/24.33

(58) Field of Classification Search .................. None
See application file for complete search history.

(56) References Cited

FOREIGN PATENT DOCUMENTS
CN    1933723 A    3/2007
CN    101343664 A    1/2009

OTHER PUBLICATIONS

Ronning et al., "Event specific real-time quantitative PCR for genetically modified Bt11 maize (*Zea mays*)," Eur. Food. Res. Technol., 2003, vol. 216, pp. 347-354.*
Qin, Wen, et al., "Quantative/Identified Detection of the Genetically Modified Maize Bt11 Components in Processed Products," Biotechnology Bulletin, 2003(6), pp. 46-50.
Wu, Mingsheng et al., "Quantitative Detection of Genetically Modified Bt176 Maize," Molecular Plant Breeding, vol. 5, No. 5, 2007, pp. 715-719.

* cited by examiner

*Primary Examiner* — Young J Kim
(74) *Attorney, Agent, or Firm* — Birch Stewart Kolasch & Birch, LLP

(57) ABSTRACT

The invention discloses a method for detection of genetically modified maize BT11. The principle of the method is that the DNA template of the sample is amplified at a temperature of 63° C.~65° C. for 45~60 min by using 4 specific primers and a DNA polymerase with strand displacement activity. The identification thereof is to make a judgment on whether BT11 component is contained in the sample by directly observing the turbidity in the reaction tube or the color change after the addition of SYBR Green with naked eyes or by agarose gel electrophoresis. The detection method of the invention has the advantages of high specificity, quickness, simplicity and convenience and the like, which provides a convenient method for detection of genetically modified maize BT11 with an extensive application prospect.

5 Claims, 2 Drawing Sheets

METHOD FOR DETECTION OF GENETICALLY MODIFIED MAIZE BT11

FIELD OF THE INVENTION

The present invention belongs to the field of molecular biotechnology, which relates to the method for detection of genetically modified organisms. Particularly, a method is disclosed for fast detection of genetically modified maize BT11, which is making a judgment on amplification by observing the turbidity in the reaction tube or observing the color change after the addition of 1000× SYBR Green with naked eyes or observing the result from agarose gel electrophoresis.

BACKGROUND OF THE INVENTION

With the rapid development of biotechnology, genetic engineering technology has provided a new approach for supply of human food and animal feed. Presently, most of the projects of genetically modified plants worldwide, which have been commercialized and are under study, are in association with food and feed, in which mature techniques have been developed for a totality of dozens of varieties, hundreds of lines, mainly including soybean, maize, rapeseed, potato, tomato, wheat and the like. Maize is one of the important food crops in the world, and the hazards faced during its process of growth are primarily from disease and insect pests, secondly from weeds. According to statistics, not spraying pesticide to maize may lead to 59% of production loss. Therefore, the earliest application of genetic engineering technology in maize is to develop genetically modified maize lines having insect-resistant and herbicide-resistant characteristics. The number of genetically modified maize lines registered in the Organization for Economic Cooperation and Development (OECD) in 2000 was 18 in total, of which improved properties were insect-resistance and herbicide-tolerance etc. In 2000, among all of the genetically modified maize cultivated in the United States, 72% were of insect-resistant characteristic, 24% were of herbicide-tolerant characteristic, whereas 4% were of insect-resistant and herbicide-tolerant characteristics in both.

Genetically modified maize BT11 is a line having simultaneously both insect-resistant and herbicide-tolerant characteristics. The insect-resistant gene transferred in it is the insect-resistant gene CrylAb of the series of BT toxic protein gene and the Glufosinate herbicide-tolerant gene transferred is Glufosinate acetyl transferase gene.

As great quantities of genetically modified crops are entering the market progressively, the safety issues of genetically modified crops and food processed from genetically modified crops have begun to be concerned by people. Essentially, there is no difference between the genetically modified crop varieties and conventionally bred crop varieties. Conventional breeding is generally realized through sexual hybridization, whereas the plant genetic engineering is to introduce exogenous recombinant DNA to the plant genome by using the techniques of agrobacteria, gene gun, Electroporation and microinjection and so on. Although theoretically speaking, the genetic characteristic and phenotype of the transferred gene may be predicted more precisely with a safer application, it is necessary at all to conduct safety assessment on genetically modified crops yet.

The European Union is the first to put forward conducting labeling administration for genetically modified food. In 1999, the non-genetically modified organisms exported to the European Union were required that should not contain pollution of more than 1% of genetically modified food; in 2002, the minimal labeling limitation was decreased to 0.9% by the European Union. Different minimal content of genetically modified component were prescribed in Japan, Australian and New Zealand, with different thresholds in the range from 1% to 5%.

In China, "Biosafety Administration Regulations on Agricultural Genetically modified Organisms" was issued and implemented on May 9, 2001, three follow-up management regulations for biosafety evaluation, labeling administration and safety administration on imported products for agricultural genetically modified organisms were issued on Jan. 5, 2002, which determined the first list of agricultural genetically modified organisms applied labeling administration, and were formally coming into force from Mar. 20, 2002.

At present, the detection of genetically modified crops mostly includes two approaches: the first, to detect whether exogenous genes (DNA) are contained. This approach mainly bases on PCR technology and hybridizing test technology of nucleic acid probes which can detect whether exogenous genes (including target genes, label genes and primers) are contained in the GMC precisely and rapidly; the second is to detect if there is exogenous protein (the product of gene expression), and this approach mainly adopts the methods of chemical analysis, gel electrophoresis and enzyme linked immunity with a comparably detailed and complicated detection work. Among these approaches, PCR detection methods are principal methods for detection of genetically modified crops, including Qualitative PCR method, Multiplex PCR method, Nested PCR method, Competitive Quantitative PCR method, Fluorescence Quantitative PCR method and the like. The Qualitative PCR and Real-Time Quantitative PCR detection methods are popularized and employed at home and abroad.

The general detection procedure of PCR amplification technique is as follows: the extraction of plant genome DNA→PCR amplification→enzymatic cleavage experiment→detection of target gene→detection report. Major apparatuses and equipments for detection are PCR equipment, electrophoresis apparatus, frozen centrifuge, Ultraviolet observing (or imaging) equipment etc. In addition, the technical conditions required for detection of genetically modified organisms are comparatively high, the apparatuses and equipments are relatively costly, as well as the cost and fee of detection are quite high.

DISCLOSURE OF THE INVENTION

The present invention is intended to disclose a method for fast detection of genetically modified maize BT11, which comprises amplifying the sequence with a set of primers designed according to the sequence where the exogenous genes and endogenous gene joined, and making a judgment on amplification through observing the turbidity or observing the color change after the addition of SYBR Green with naked eyes, or observing the results from agarose gel electrophoresis.

The technical solution according to the present invention is as follows:

A set of specific primer which are used in the detection of genetically modified maize BT11, wherein the sequences of the primer are:

```
the outer primer forward sequence:
                                        (SEQ ID NO: 1)
5'-AGGGATTCTTGGATTTTTGG-3';

the outer primer reverse sequence:
                                        (SEQ ID NO: 2)
5'-AGAAATGGTTTCCACCAGAA-3';
```

-continued the inner primer forward sequence:
(SEQ ID NO: 3)
5'-ATGAAAATAGCCATGAGCGACCATCCATTTCTTGGTCTAAAATCTG
T-3';

the inner primer reverse sequence:
(SEQ ID NO: 4)
5'-GGCCATTTATCATCGACCAGAGGAATGTAATCTATGGCAAGGA
A-3'.

Each primer is independently prepared into a mother liquor with a concentration of 100 μmol/L. Take 1 μL of each outer primer solution, 8 μL of each inner primer solution, 2 μL of sterile deionized water, mix thoroughly, and then get a mixed solution of primers.

The method of the present invention for fast detection of genetically modified maize BT11 with the set of primers described above comprises steps as follows:

(1) The amplification is performed at 63-65° C. for 45-60 min by using 4 specific primers according to claim 1 and one DNA polymerase with strand displacement activity with the addition of the template DNA, afterwards the reaction system is incubated at 80° C. for 2 min and stored at 4° C. The amplification reaction system is: the total volume of amplification reaction is 25 μL comprising 2.5 μL of 10× ThermoPol Buffer, 6.25 μL of 4 mol/L Betaine, 0.25 μL of 0.2 mol/L MgSO4, 1 μL of mixed solution of primers, 3.5 μL of 10 μmol/L dNTPs, 1-2 μL of DNA polymerase with strand displacement activity and 1-5 μL of the template DNA, which is supplemented with sterile deionized water to 25 μL. The system is mixed thoroughly, and performed on the machine after being centrifuged at 4000-8000 rpm for 5-10 seconds;

(2) When the amplification reaction is complete, take 3-25 μL of reaction product, and judge whether it is amplified or not by using different methods, including: directly adding fluorescent dye SYBR Green to the amplification tube and observing whether it is amplified through the color change; or observing the amplification by assessing the amount of the white sediment of magnesium pyrophosphate, which is a byproduct of the amplification; and or judging the amplification results by observing the bands produced during the agarose gel electrophoresis.

The said DNA polymerase with strand displacement activity used in the detection method of the present invention is 1-2 μL of the 8000 U/L Bst DNA polymerase large fragment.

The volume of the said fluorescent dye SYBR Green added according to the present invention is 1-2 μL, and the concentration of which is 1000 times.

The template DNA according to the detection method of the present invention refers to the genome DNA extracted from samples to be detected.

In order that the detection method of the present invention could be set forth more clearly, now the experiment method of the invention will be illustrated in detail as follows.

1. Principle

The present method applies a new type of method for nucleic acid amplification, the principle of which is that the nucleic acid is amplified at 63° C.-65° C. by using 4 specific primers and a DNA polymerase with strand displacement activity, and the amplification efficiency can achieve a copy number of $10^9$-$10^{10}$ in short time. The method has the advantages of high specificity, quickness, simplicity and convenience, readily detection and the like.

2. Design of Primers 4 primers are designed according to the sequence where the exogenous gene and endogenous gene joined in the genetically modified maize BT11. The primers are synthesized by Sangon. Ltd., Shanghai.

TABLE 1

PRIMER SEQUENCE USED

| PRIMER | BASE NUMBER | SEQUENCE(5' to 3') |
|---|---|---|
| BT11 Forward Outer Primer | 20 | AGGGATTCTTGGATTTTTGG (SEQ ID NO: 1) |
| BT11 Reverse Outer Primer | 20 | AGAAATGGTTTCCACCAGAA (SEQ ID NO: 2) |
| BT11 Forward Inner Primer | 47 | ATGAAAATAGCCATGAGCGAC CATCCATTTCTTGGTCTAAAAT CTGT (SEQ ID NO: 3) |
| BT11 Reverse Inner Primer | 44 | GGCCATTTATCATCGACCAGAGGAA TGTAATCTATGGCAAGGAA (SEQ ID NO: 4) |

3. Reaction Conditions

The reaction reagents needed include DNA polymerase with strand displacement activity, dNTPs, specific primers for genetically modified maize BT11, Betaine, MgSO₄ and reaction buffers. The reaction is performed under the condition of constant temperature, and the reaction time may vary depending on the efficiency of primers and the quality of the template DNA, which is generally 1 h or less. The amplification is performed at 63-65° C. for 45-60 min with the addition of the template DNA, afterwards the reaction system is incubated at 80° C. for 2 min till ending.

The advantage of this technology lie in that the thermal cycle is not needed during the course of reaction, so that those expensive equipments, such as PCR equipment, are not required, and the reaction temperature can be maintained only by thermostat water bath or metal heating blocks.

Materials and Methods:

(1) Reagents: BioLabs Bst DNA polymerase large fragment (available from NEW ENGLAND) and 10× ThermoPol Buffer solution; specific primers for BT11; solution of Betaine; solution of MgSO₄; dNTPs;

(2) Amplification reaction system: the total volume of amplification reaction is 25 μL comprising 2.5 μL of 10× ThermoPol Buffer, 6.25 μL of 4 mol/L Betaine, 0.25 μL of 0.2 mol/L MgSO₄, 1 μL of the mixed solution of primers, 3.5 μL of 10 μmol/L dNTPs, 1-2 μL of 8000 U/L Bst DNA polymerase large fragment, 1-5 μL of the template DNA, which is supplemented with sterile deionized water to 25 μL. The system is mixed thoroughly, and performed on the machine after being centrifuged at 4000-8000 rpm for 5-10 seconds;

(3) Course of amplification reaction: the amplification is performed at 63-65° C. for 45-60 min, afterwards the system is incubated at 80° C. for 2 min and stored at 4° C.;

(4) When the amplification reaction is complete, take 3-25 μL of the reaction product for judging whether it is amplified or not by using different detection methods.

4. Observation of the Amplification Results

There are three methods for observation which are suitable to be conducted under different conditions:

(1) Use 2% agarose gel, add EB staining agent to the agarose gel and carry out electrophoresis at 100V for 50 min. The result is observed under an ultraviolet lamp. Due to the different lengths of stem-loop structure produced during the amplification reaction, appearance of scattering bands and ladder-like bands beginning from the loading wells can be shown in the electrophoretogram. The result is shown in FIG. 1.

(2) Owing to the large amount of double-stranded DNA products through the reaction, therefore, fluorescent dye SYBR Green can be added directly to the amplification tube. What can be observed with naked eyes is that the reaction tube hasn't performed amplification appears to be orange, whereas the reaction tube has performed amplification turns into green. This result is shown in FIG. 2.

(3) The detection can also be performed by assessing the amount of the white sediment of the magnesium pyrophosphate, which is a byproduct of amplification. The byproduct magnesium pyrophosphate is generated during the reaction when the nucleic acids are synthesized enormously. Whether the amplification being performed or not can be judged by detecting the turbidity in the reaction tube with naked eyes or by using turbidity meter.

The advantages of the amplification method of the present invention used for detection of genetically modified maize BT11 lie in the following aspects:

(1) Easy operation: the reaction can be performed only at one constant temperature, without the need of complicated equipments.
(2) High specificity: 6 regions of the target sequence are amplified by 4 primers, which impart a high specificity to the technique.
(3) Quickness and high efficiency: the whole amplification reaction can be completed within less than 1 h with a production of copy number of up to $10^9$-$10^{10}$.
(4) Simple and convenient detection: the amplification is performed whether or not can be judged through directly observing the turbidity of the sediments in the reaction tube or through the color change of SYBR Green with naked eyes.

EXAMPLES

In order that the detection method of the present invention could be set forth more clearly, now the experiment method of the invention will be illustrated in detail as follows. What should be illustrated is that the sequences of the primers described in the present invention are shown in Table 1.

Example 1

Figure 1:
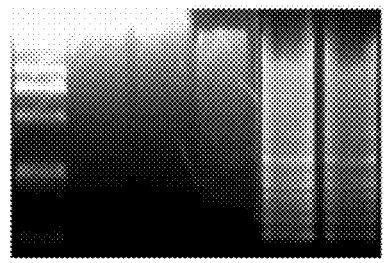
FIG. 1 is an electrophoretogram of the amplification products, in which, from the left to the right are Marker, blank control, negative control, negative sample, positive control and positive sample successively.
Figure 2:
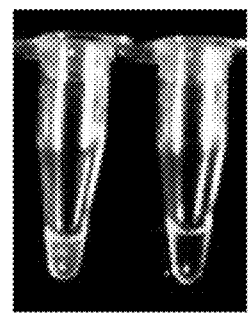
FIG. 2 is a graph showing the results after the addition of SYBR Green to the amplification products, in which the left is positive control, whereas the right is negative control.
Figure 3:
FIG. 3 is a graph showing the results after the addition of SYBR Green to the amplification products, in which, from the left to the right are negative control, positive control and positive sample successively.

(1) Reagents: Bst DNA polymerase large fragment available from BioLabs (NEW ENGLAND) and 10× ThermoPol Buffer solution; mixed solution of specific primers; 4 mol/L Betaine solution and 0.2 mol/L MgSO4 solution.
(2) Amplification reaction system: the total volume of amplification reaction was 25 µL comprising 2.5 µL of 10× ThermoPol Buffer, 6.25 µL of 4 mol/L Betaine, 0.25 µL of 0.2 mol/L $MgSO_4$, 1 µL of the mixed solution of primers, 3.5 µL of 10 µmol/L dNTPs, 1 µL of 8000 U/L Bst DNA polymerase large fragment, 1 µL of the template DNA, which was supplemented with sterile deionized water to 25 µL. The system was mixed thoroughly, and performed on the machine after being centrifuged at 4000 rpm for 5 seconds.
(3) Amplification reaction procedure: the amplification was performed at 63° C. for 60 min, afterwards the system was incubated at 80° C. for 2 min and stored at 4° C.
(4) When the amplification reaction was complete, took 15 µL of the reaction product, directly added 1 µL of the fluorescent dye 1000× SYBR Green to the reaction tube, mixed by oscillating and observed the results with naked eyes. The reaction tube hadn't performed amplification reaction appeared to be orange; whereas the reaction tube had performed amplification reaction turned into green. The result was illustrated in FIG. 3 showing that the sample to be detected was positive sample which contained the component of genetically modified maize BT11.

Example 2

Figure 4:
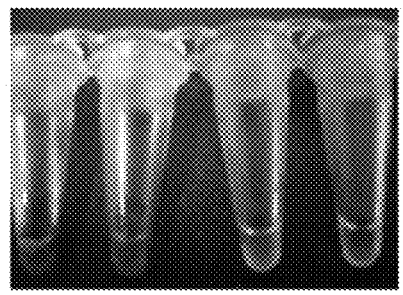
FIG. 4 is a graph showing the results after the addition of SYBR Green to the amplification products, in which, from the left to the right are negative control, positive control, sample 1 to be detected and sample 2 to be detected successively.

(1) Reagents: Bst DNA polymerase large fragment available from BioLabs (NEW ENGLAND) and 10× ThermoPol Buffer solution; mixed solution of specific primers of BT11; 4 mol/L Betaine solution and 0.2 mol/L $MgSO_4$ solution.
(2) Amplification reaction system: the total volume of amplification reaction is 25 µL comprising 2.5 µL of 10× ThermoPol Buffer, 6.25 µL of 4 mol/L Betaine, 0.2 mol/L $MgSO_4$, 0.25 µL of the mixed solution of primers, 3.5 µL of 10 µmol/L dNTPs, 2 µL of 8000 U/L Bst DNA polymerase large fragment, 2 µL of the template DNA, which was supplemented with sterile deionized water to 25 µL. The system was mixed thoroughly, and performed on the machine after being centrifuged at 8000 rpm for 10 seconds.
(3) Amplification reaction procedure: the amplification was performed at 65° C. for 45 min, afterwards the system was incubated at 80° C. for 2 min and stored at 4° C.
(4) When the amplification reaction was complete, took 15 µL of the reaction product, added 2 µL of the fluorescent dye 1000× SYBR Green to the reaction tube, mixed by oscillating and observed the results with naked eyes. The reaction tube hadn't performed amplification reaction appeared to be orange, whereas the reaction tube had performed amplification reaction turned into green. The result was illustrated in FIG. 4 showing that sample 1 to be detected was positive sample that contained the component of genetically modified maize BT11, whereas sample 2 contained no component of genetically modified maize BT11.

Example 3

Figure 5:
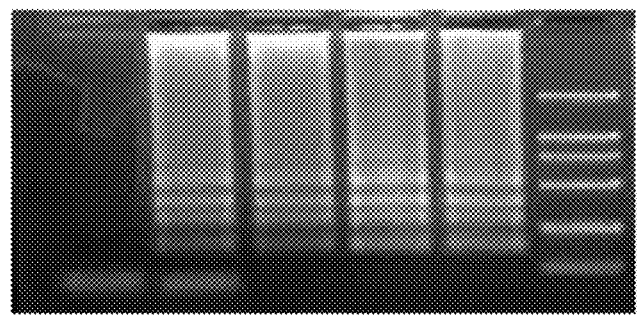
FIG. 5 is an electrophoretogram of the amplification products, in which, from the left to the right are negative control, positive control, sample 1 to be detected, sample 2 to be detected, sample 3 to be detected and DL2000 DNA Marker successively.

(1) Reagents: Bst DNA polymerase large fragment available from BioLabs (NEW ENGLAND) and 10× ThermoPol Buffer solution; mixed solution of specific primers; 4 mol/L Betaine solution and 0.2 mol/L MgSO4 solution.
(2) Amplification reaction system: the total volume of amplification reaction was 25 μL comprising 2.5 μL of 10× ThermoPol Buffer, 6.25 μL of 4 mol/L Betaine, 0.2 mol/L MgSO$_4$, 0.25 μL of the mixed solution of primers, 3.5 μL of 10 μmol/L dNTPs, 2 μL of 8000 U/L Bst DNA polymerase large fragment, 5 μL of the template DNA, which was supplemented with sterile deionized water to 25 μL. The system was mixed thoroughly, and performed on the machine after being centrifuged at 8000 rpm for 10 seconds.
(3) Amplification reaction procedure: the amplification was performed at 63° C. for 60 min, afterwards the system was incubated at 80° C. for 2 min and stored at 4° C.
(4) When the amplification reactions was completed, took 25 μL of the reaction products to make analysis by 2% agarose gel electrophoresis and observed the results under an ultraviolet lamp. Product from the reaction tube hadn't performed amplification reaction didn't produce obvious bands, and product from the reaction tube had performed amplification reaction produced ladder-like bands. The result was shown in FIG. 5 showing that all of the three samples contained the component of genetically modified maize BT11.

Example 4

Figure 6:
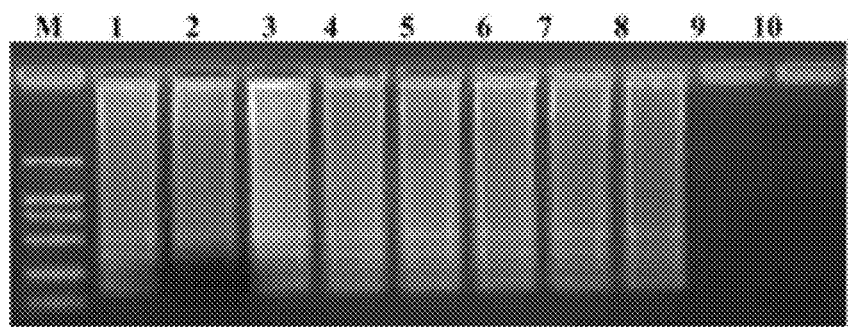
FIG. 6 is an agarose gel electrophoretogram of the amplification products from example 4 using the method of the present invention. The result is observed under an ultraviolet lamp, wherein M, DL2000 DNA, Marker; 1, 5%; 2, 1%; 3, 0.5%; 4, 0.1%; 5, 0.05%; 6, 0.01%; 7, 0.005%; 8, 0.001%; 9, 0.0005%; 10, negative control.
Figure 7:
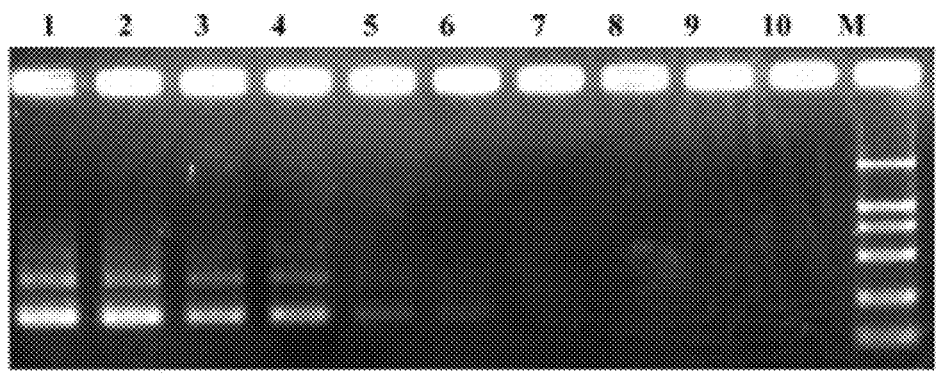
FIG. 7 is an agarose gel electrophoretogram of the amplification products from example 4 using the conventional Qualitative PCR method. The result is observed under an ultraviolet lamp, wherein, M, DL2000 DNA, Marker; 1, 5%; 2, 1%; 3, 0.5%; 4, 0.1%; 5, 0.05%; 6, 0.01%; 7, 0.005%; 8, 0.001%; 9, 0.0005%; 10, negative control.

Contrast experiment: contrast of the qualitative PCR detection method and the detection method of the present invention for genetically modified maize BT11:
(1) Reagents used in the method of the present invention: Bst DNA polymerase large fragment available from BioLabs (NEW ENGLAND) and 10× ThermoPol Buffer solution; mixed solution of specific primers; 4 mol/L Betaine solution; 0.2 mol/L MgSO4 solution; template DNA form samples containing components of genetically modified maize BT11 which percentages contributed to 5%, 1%, 0.5%, 0.1%, 0.05%, 0.01%, 0.005%, 0.001%, 0.0005% and 0% independently.
(2) Amplification reaction system of the present invention: the total volume of amplification reaction was 25 μL comprising 2.5 μL of 10× ThermoPol Buffer, 6.25 μL of 4 mol/L Betaine, 0.25 μL of 0.2 mol/L MgSO$_4$, 1 μL of the mixed solution of primers, 3.5 μL of 10 μmol/L dNTPs, 2 μL of 8000 U/L Bst DNA polymerase large fragment, 5 μL, of the template DNA, which was supplemented with sterile deionized water to 25 μL. The system was mixed thoroughly, and performed on the machine after being centrifuged at 8000 rpm for 10 seconds.
(3) Amplification reaction procedure of the present invention: the amplification was performed at 63° C. for 60 min, afterwards the system was incubated at 80° C. for 2 min and stored at 4° C.
(4) When the amplification reaction was complete, took 4 μL of the reaction products to make analysis by agarose gel electrophoresis and observed the results under an ultraviolet lamp. Product from the reaction tube hadn't performed amplification reaction didn't produce obvious bands, and product from the reaction tube had performed amplification reaction produced ladder-like bands. The result was shown in FIG. 6, wherein: M, DL2000 DNA, Marker; 1, 5%; 2, 1%; 3, 0.5%; 4, 0.1%; 5, 0.05%; 6, 0.01%; 7, 0.005%; 8, 0.001%; 9, 0.0005%; 10, negative control.
(5) Method of PCR: the target gene was amplified with a pair of outer primers from the reaction of the present invention. The PCR reaction was a system of 25 μL comprising 2.5 μL of 10× PCR buffer (Promega), 0.5 μL of 10 mM dNTPs (Promega), 0.5 μL each of forward primer and reverse primer (10 mM), 0.5 μL of Taq enzyme (5 U/μL, Promega), 1 uL of the template DNA and 19.5 uL of the sterile deionized water. PCRs were performed as follows: the initial denaturation was at 95° C. for 5 min, followed by 35 cycles of denaturation at 95° C. for 30 s, annealing at 52° C. for 30 s and extension at 72° C. for 30 s. After the last cycle, the systems were incubated at 72° C. for 7 min. 10 uL of PCR products were taken to be electrophoresed on 2% agarose gel at 100V for 40 min and observed the result through a gel image analyzing system. The result was shown in FIG. 7, wherein: M, DL2000 DNA, Marker; 1, 5%; 2, 1%; 3, 0.5%; 4, 0.1%; 5, 0.05%; 6, 0.01%; 7, 0.005%; 8, 0.001%; 9, 0.0005%; 10, negative control.

It can be concluded from the contrast of the two methods that the susceptibility of the method of the present invention was obviously higher than that of the PCR method, which can detect samples containing much less amounts of component of genetically modified maize BT11.

With detailed illustration of the preferred embodiments, those skilled in the art will clearly understand that, various changes and modifications can be practiced without departing from the scope and spirit of the application patent described above, and any simple amendments, equivalent changes and modifications to the embodiments aforementioned according to the principle features of the present invention will fall within the scope of the technical solutions of the present invention. In addition, the present invention is not limited by the exemplary embodiments discussed in the specification herein either.

What is claimed is:

1. Specific primers used for detecting genetically modified maize BT11, comprising:

```
the outer primer forward sequence:
                                       (SEQ ID NO: 1)
5'-AGGGATTCTTGGATTTTTGG-3';

the outer primer reverse sequence:
                                       (SEQ ID NO: 2)
5'-AGAAATGGTTTCCACCAGAA-3';

the inner primer forward sequence:
                                       (SEQ ID NO: 3)
5'-ATGAAAATAGCCATGAGCGACCATCCATTTCTTGGTCTAAAATCTG
T-3'; and the inner primer reverse sequence:
                                       (SEQ ID NO: 4)
5'-GGCCATTTATCATCGACCAGAGGAATGTAATCTATGGCAAGGA
A-3'.
```

2. A method for detecting genetically modified maize BT11, which method comprises the steps as follows:
    (a) performing an amplification reaction at 63°-65° C. for 45-60 minutes using an amplification reaction system, wherein the amplification reaction system comprises: 2.5 μL of 10× ThermoPol Buffer, 6.25 μL of 4 mol/L Betaine, 0.25 μL of 0.2 mol/L MgSO$_4$, 1 μL of the specific primers of claim 1, 3.5 μL of 10 μmol/L dNTPs, 1-2 μL of DNA polymerase with strand displacement activity, 1-5 μL of a template DNA, and the amplification reaction system is supplemented with sterile deionized water to a total volume of 25 μL; the resulting amplification reaction system being thoroughly mixed and centrifuged at 4000-8000 rpm for 5-10 seconds;
    (b) incubating the amplification reaction system at 80° C. for 2 minutes and storing at 4° C.;
    (c) sampling 3-25 μL of the reaction product of (b) to determine whether the amplification reaction has occurred or not by using a method selected from the group consisting of:
        (i) directly adding a fluorescent dye, SYBR GREEN, to the amplification tube and then determining whether the amplification reaction occurs or not by observing a color change;
        (ii) assessing the amount of a white sediment of magnesium pyrophosphate, which is a byproduct of the amplification; and
        (iii) observing bands in an agarose gel electrophoresis.

3. The method for detecting of genetically modified maize BT11 according to claim 2, wherein said specific primers are prepared as follows:
    each primer is independently prepared as a master mix solution with a concentration of 100 μmol/L and 1 μL of each outer primer master mix solution, 8 μL of each inner primer master mix solution, and 2 μL of sterile deionized water are thoroughly mixed.

4. The method for detection of genetically modified maize BT11 according to claim 2, wherein a concentration of the fluorescent dye SYBR Green is 1000× SYBR Green, and the added volume of the fluorescent dye SYBR Green is 1-2 μL.

5. A method for detection of genetically modified maize BT11 according to claim 2, wherein 1-2 μL of 8000 U/L Bst DNA polymerase large fragment is used as the DNA polymerase with strand displacement activity.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 1
agggattctt ggatttttgg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
agaaatggtt tccaccagaa                                               20

<210> SEQ ID NO 3
<211> LENGTH: 47
<212> TYPE: DNA
<213> ORGANISM: Artificial Sequence
<220> FEATURE:
<223> OTHER INFORMATION: Synthetic primer

<400> SEQUENCE: 3
atgaaaatag ccatgagcga ccatccattt cttggtctaa aatctgt                 47

<210> SEQ ID NO 4
<211> LENGTH: 44
<212> TYPE: DNA
<213> ORGANISM: Artificial Sequence
<220> FEATURE:
<223> OTHER INFORMATION: Synthetic primer

<400> SEQUENCE: 4
ggccatttat catcgaccag aggaatgtaa tctatggcaa ggaa                    44
```